United States Patent
McLaughlin et al.

(10) Patent No.: US 9,409,927 B2
(45) Date of Patent: Aug. 9, 2016

(54) SUPER LEWIS ACIDIC BORATE ESTERS AS 18F-LABELED PET PROBES

(71) Applicants: UNIVERSITY OF SOUTH FLORIDA, Tampa, FL (US); H. LEE MOFFITT CANCER CENTER AND RESEARCH INSTITUTE, INC., Tampa, FL (US)

(72) Inventors: Mark Lee McLaughlin, Tampa, FL (US); Haibin Tian, Tampa, FL (US)

(73) Assignees: H. Lee Moffitt Cancer Center and Research Institute, Inc., Tampa, FL (US); University of South Florida, Tampa, FL (US)

(*) Notice: Subject to any disclaimer, the term of this patent is extended or adjusted under 35 U.S.C. 154(b) by 0 days.

(21) Appl. No.: 14/762,544

(22) PCT Filed: Jan. 24, 2014

(86) PCT No.: PCT/US2014/013055
§ 371 (c)(1),
(2) Date: Jul. 22, 2015

(87) PCT Pub. No.: WO2014/117028
PCT Pub. Date: Jul. 31, 2014

(65) Prior Publication Data
US 2015/0361110 A1    Dec. 17, 2015

Related U.S. Application Data

(60) Provisional application No. 61/756,075, filed on Jan. 24, 2013.

(51) Int. Cl.
C07F 5/04      (2006.01)
C07B 59/00   (2006.01)
C07K 7/56     (2006.01)

(52) U.S. Cl.
CPC . *C07F 5/04* (2013.01); *C07B 59/00* (2013.01); *C07B 59/004* (2013.01); *C07B 59/008* (2013.01); *C07K 7/56* (2013.01); *C07B 2200/05* (2013.01)

(58) Field of Classification Search
CPC .................................. C07F 5/04; C07B 59/00
See application file for complete search history.

(56) References Cited

U.S. PATENT DOCUMENTS

| | | | |
|---|---|---|---|
| 2,909,560 A | 10/1959 | McManimie | |
| 8,207,337 B2 | 6/2012 | Miyaura et al. | |
| 8,563,761 B2 * | 10/2013 | Armand | C07F 5/022 423/472 |
| 2011/0171112 A1 | 7/2011 | Armand et al. | |

FOREIGN PATENT DOCUMENTS

WO     2013012754 A1     1/2013

OTHER PUBLICATIONS

International Search Report and Written Opinion for Application No. 14/13055, mailed May 13, 2014.
International Preliminary Report on Patentability for PCT/US14/13055, mailed Aug. 6, 2015.
Taylor, et al., "Triol Borates and Aminoalcohol derivates of Boric Acid: Their Formation and Hydrolysis", Polyhedron 15 (19), 1996.
Ting, et al., "Fast 18F Labeling of a Near-Infrared Fluorophore Enables Positron Emission Tomography and Optical Imaging of Sentinel Lymph Nodes", Bioconjugate Chem. vol. 21, 2010.
Yamamoto, et al., "Cyclic Triolborates: Air- and Water-Stable Ate Complexes of Organoboronic Acids", Angew. Chem. vol. 120, 2008.

\* cited by examiner

*Primary Examiner* — Golam M M Shameem
(74) *Attorney, Agent, or Firm* — Meunier Carlin & Curfman LLC

(57) ABSTRACT

Compounds having a 1-bora-1-fluoro-2,6,7-trioxabicyclo[2.2.2]octane moiety wherein the fluorine is $^{18}F$ are described. Also described are reagents for radiolabeling a molecule having Formula I. Method for radiolabeling molecules with the disclosed reagents are also descried, as are radiolabeled molecules prepared thereby.

11 Claims, 8 Drawing Sheets

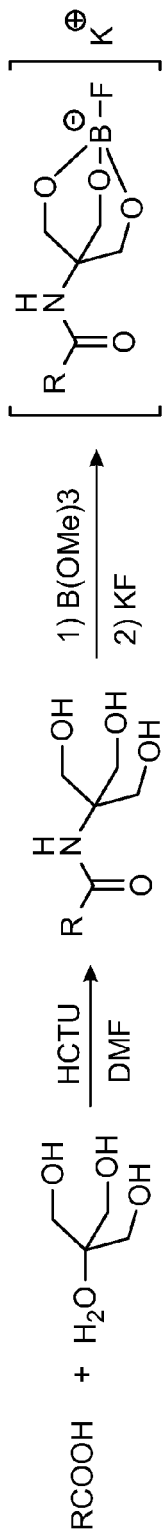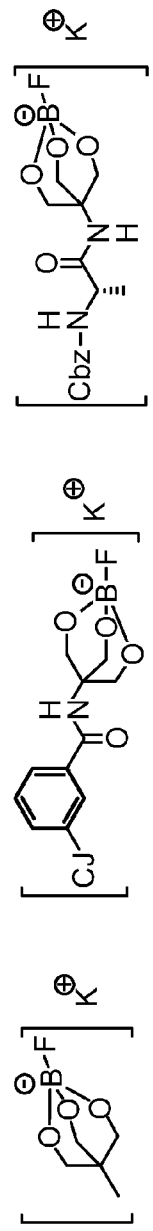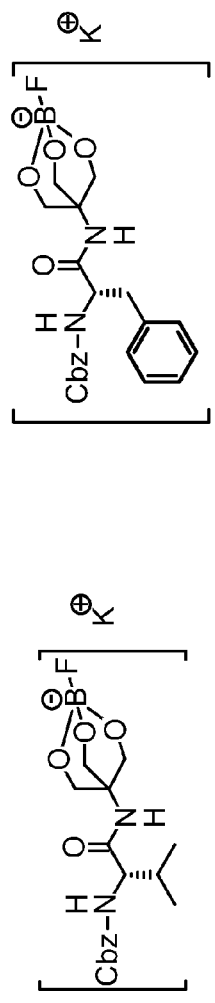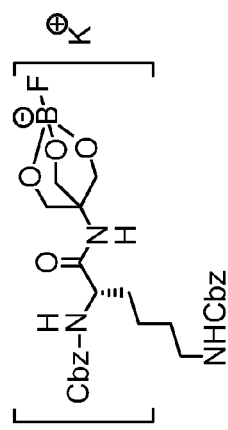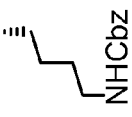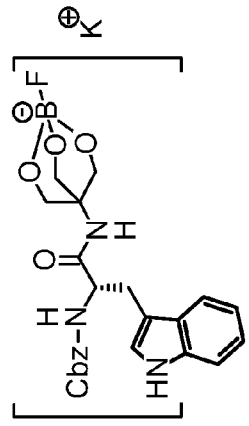
FIG. 2
FIG. 3

SUPER LEWIS ACIDIC BORATE ESTERS AS 18F-LABELED PET PROBES

CROSS REFERENCE TO RELATED APPLICATIONS

This application claims the benefit of priority to U.S. Provisional Application 61/756,075, filed Jan. 24, 2013, which is incorporated by reference herein in its entirety.

ACKNOWLEDGEMENT OF GOVERNMENT SUPPORT

This invention was made with government support under Grant No. 1R43CA167998-01A1 awarded by the National Cancer Institute. The Government has certain rights in the invention.

BACKGROUND

Positron emission tomography (PET) is effective in diagnosing a variety of diseases including heart diseases and cancer. And in 2011, just under two million PET scans were performed in the US. These techniques generally involve administering an agent labeled with a radioisotope to a patient, followed by detecting γ-rays emitted directly or indirectly from the radiolabeled agent or so-called PET imaging probe.

[$^{18}$F]2-fluoro-2-deoxy-D-glucose (FDG) is one imaging probe currently used for PET examination. FDG tends to be concentrated in areas where glucose metabolism is enhanced, thereby making it possible to detect tumors with accelerated glucose metabolism. While FDG remains the "gold standard" of PET imaging probes, its low specificity may produce suboptimal results in cancer imaging aimed at detecting small tumors and micro-metastases, especially in metabolically active tissues such as brain, liver, spleen, lung, and breast, such that it may be difficult to discern a signal given the noise.

Other PET imaging probes are being developed to avoid such shortcomings or are being sought for uses in other medical indications. As such, the development of new PET imaging agents and methodologies has received great interest. The attractiveness of the market for new PET imaging probes is evidenced by several novel PET probes currently in development. For example, $^{18}$F-FLT (SNMMI) is in a Phase 4 clinical trial for targeted breast cancer imaging, $^{18}$F-FCH (SNMMI) is in a Phase 0 clinical trial for prostate cancer staging, and $^{18}$F-FAC (Sofie Biosciences) is in a Phase 1 trial for cancer. In non-cancer indications, Flurpiridaz F-18 (Lantheus) is in a phase 3 clinical trial for myocardial perfusion imaging for the detection of coronary artery disease.

One challenge of developing PET imaging probes is the speed at which the probes can be prepared. The time it takes to prepare, purify, and isolate the probe following the labeling reaction with the $^{18}$F radioisotope is critical to there being sufficient radioactivity remaining in the probe to give sufficient signal to noise ratios during the PET scan. With the half-life of $^{18}$F at 110 minutes, reaction times longer than a few minutes waste the expensive radioactivity of $^{18}$F. As an example, the preparation of an imaging probe using an established $^{18}$F-labeling isotope called 4-[$^{18}$F]fluorobenzoate-N-succinamide (SFB) takes 3 reaction steps and 80 minutes. Thus, what are needed are new $^{18}$F radiolabeling agents that can be used to rapidly radiolabel a wide variety of compounds. The compositions and methods disclosed herein address these and other needs.

SUMMARY

In accordance with the purposes of the disclosed compounds, compositions and methods, as embodied and broadly described herein, the disclosed subject matter relates to compounds, compositions and methods of making and using the compositions. In more specific aspects, the disclosed subject matter relates to compounds having the following moiety:

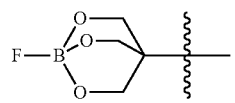

wherein the fluorine is $^{18}$F. Also disclosed are reagents for radiolabeling a molecule having Formula I:

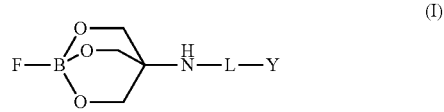

(I)

wherein F is $^{18}$F, L is a bond or a linker of from 1 to 20 atoms in length and Y is a reactive moiety capable of forming a bond with another molecule. Method for radiolabeling molecules with the disclosed reagents are also disclosed herein, as are radiolabeled molecules prepared according to the disclosed methods.

Additional advantages will be set forth in part in part in the description that follows and the Figures, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF FIGURES

The accompanying Figures, which are incorporated in and constitute a part of this specification, illustrate several aspects of the invention and together with the description serve to explain the principles of the invention.

FIG. 2 is a synthetic scheme for the preparation of generic 4-amido-1-bora-1-fluoro-2,6,7-trioxabicyclo[2.2.2]octane reagents.

FIG. 3 shows the structure of exemplary reagents containing a 1-bora-1-fluoro-2,6,7-trioxabicyclo[2.2.2]octane moiety for radiolabeling.

DETAILED DESCRIPTION

Figure 1A:
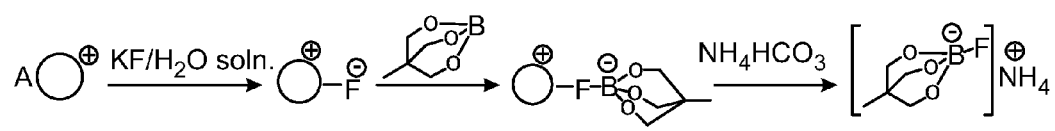
FIG. 1A is a synthetic scheme for the preparation of a 1-bora-1-fluoro-2,6,7-trioxabicyclo[2.2.2]octane reagent. The $^1$H, $^{13}$C, $^{19}$F, and $^{14}$B NMR spectra for the final product are shown in FIGS. 1B-E, respectively. The mass spectrum for the final product is shown in FIG. 1F. The elemental analysis results for the final product (run in duplicate) are shown in FIG. 1G.
Figure 1B:
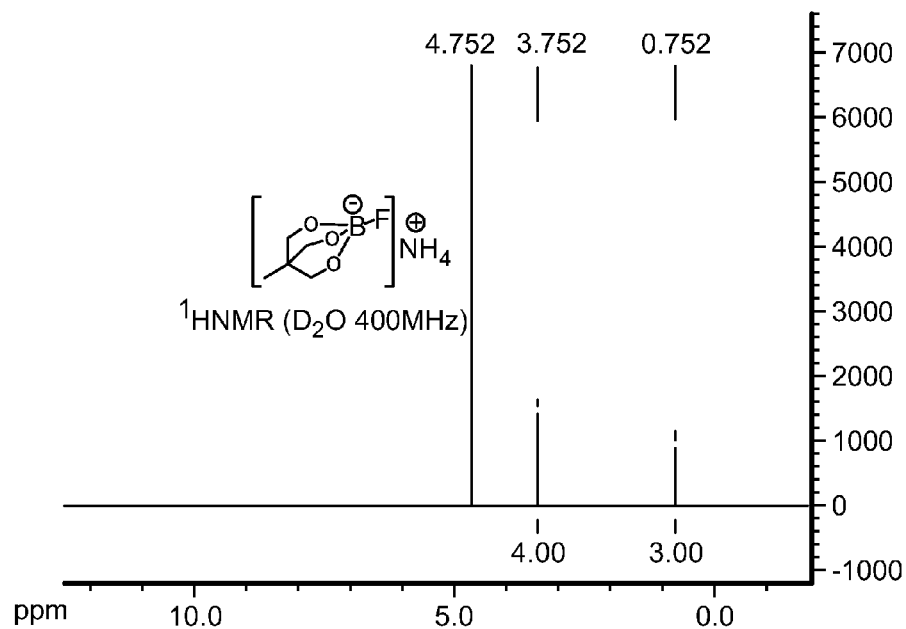
Figure 1C:
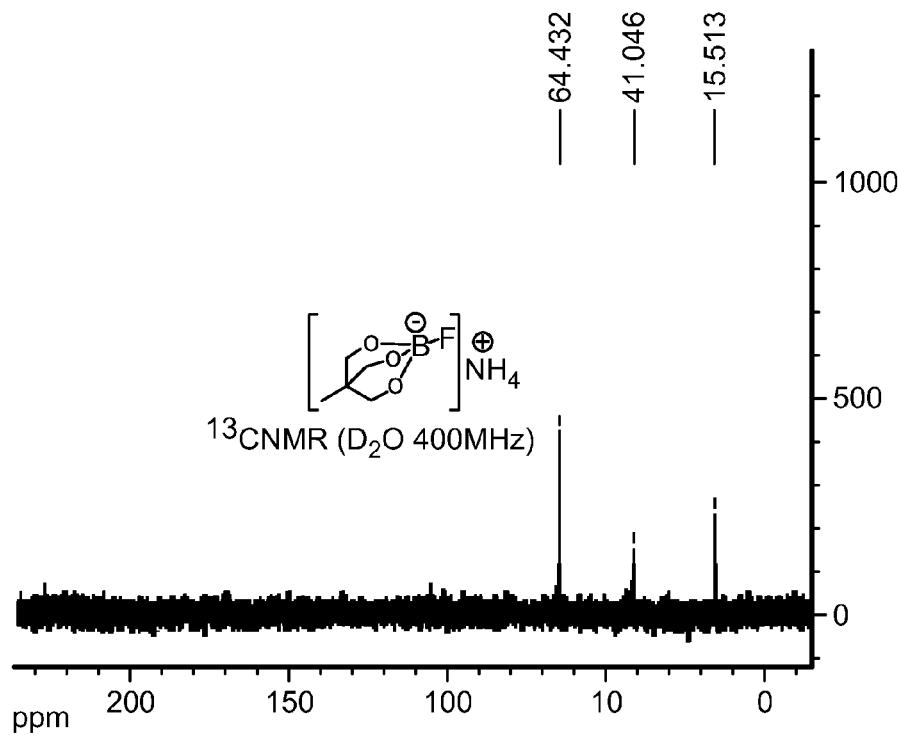
Figure 1D:
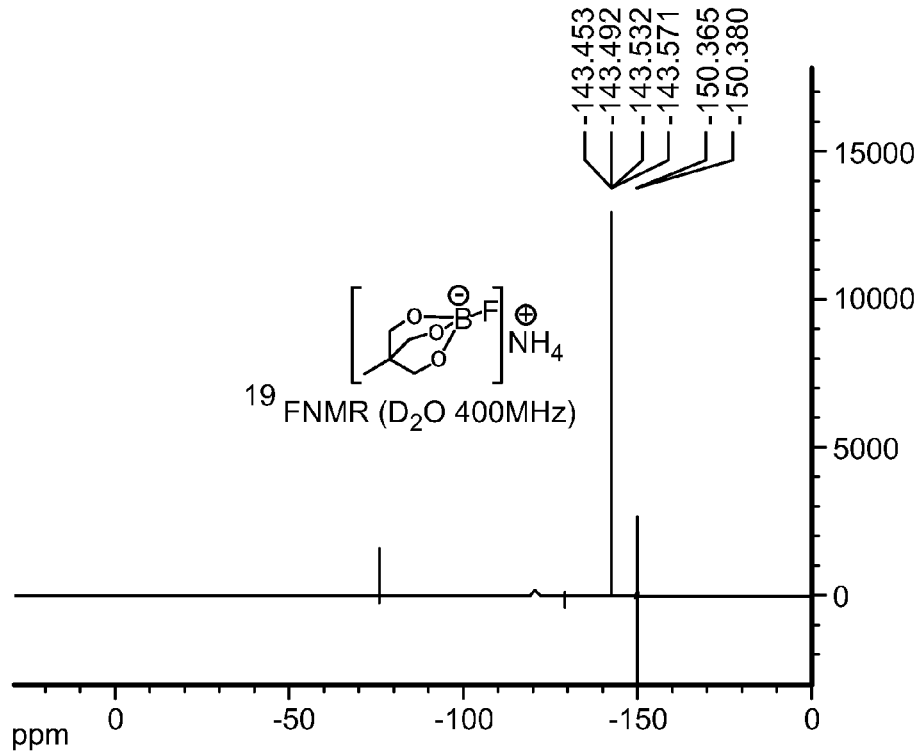
Figure 1E:
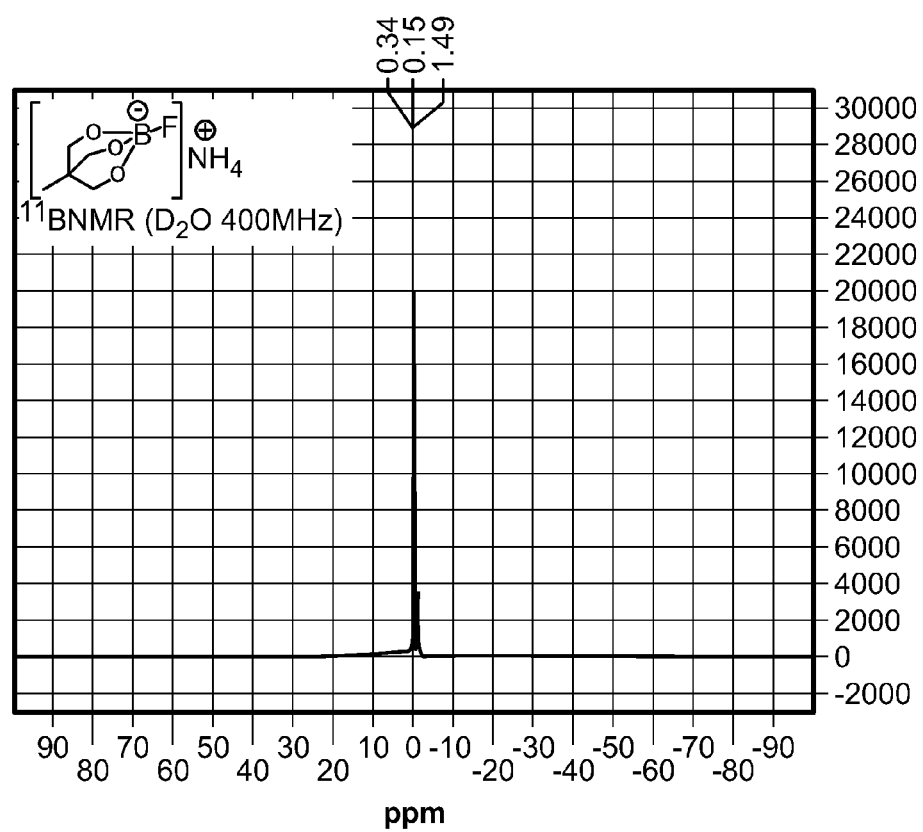
Figures 1F, 1G:
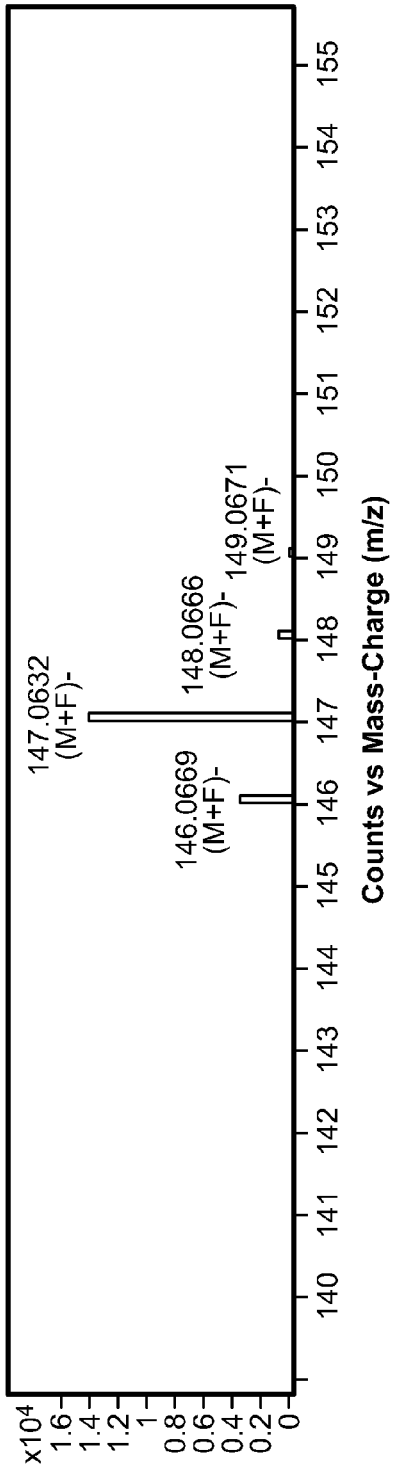
Figure 4:
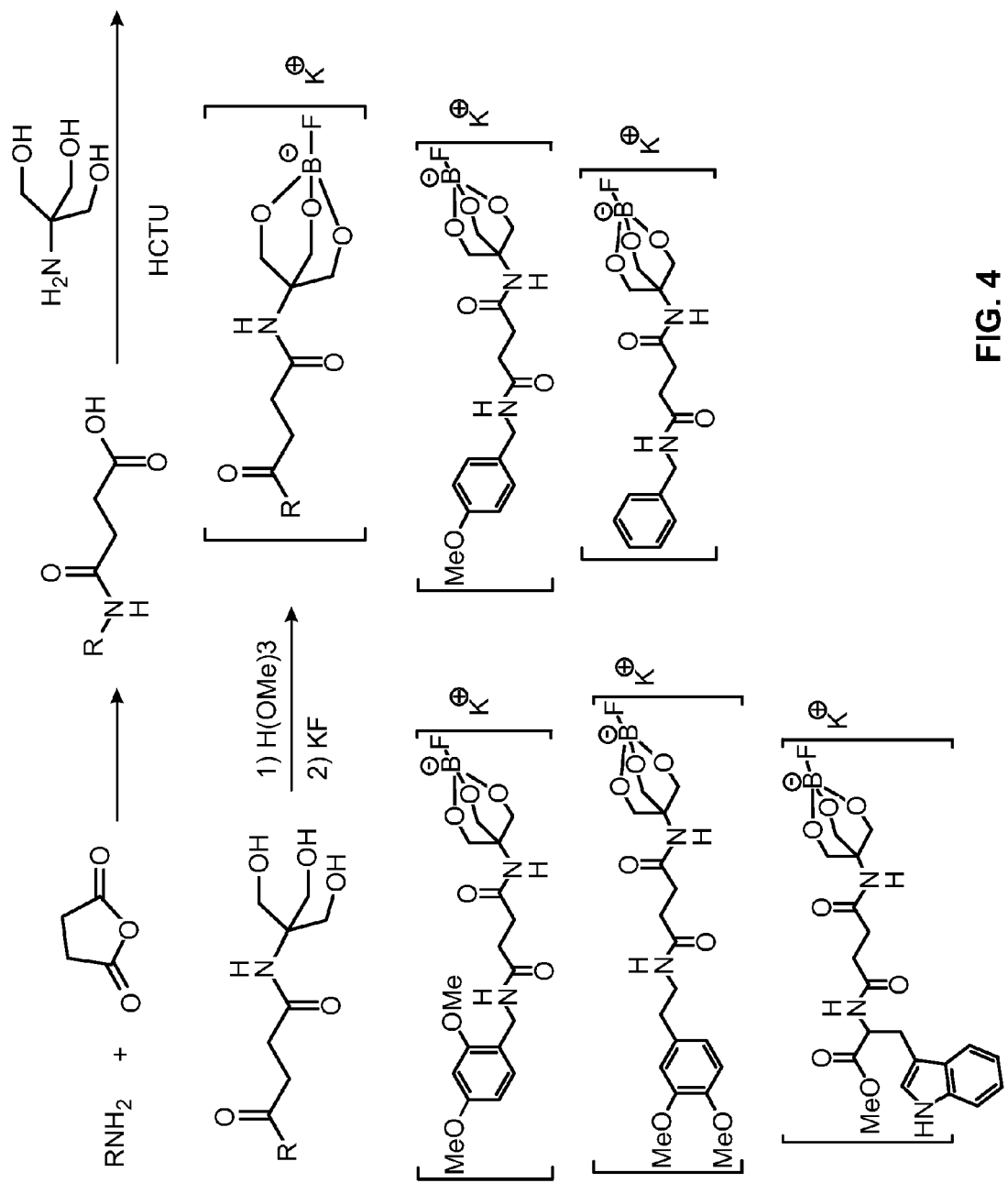
FIG. 4 is a synthetic scheme showing the synthesis of a generic 4-succinamide-1-bora-1-fluoro-2,6,7-trioxabicyclo[2.2.2]octane reagents for radiolabeling and structures of exemplary reagents.
Figure 5:
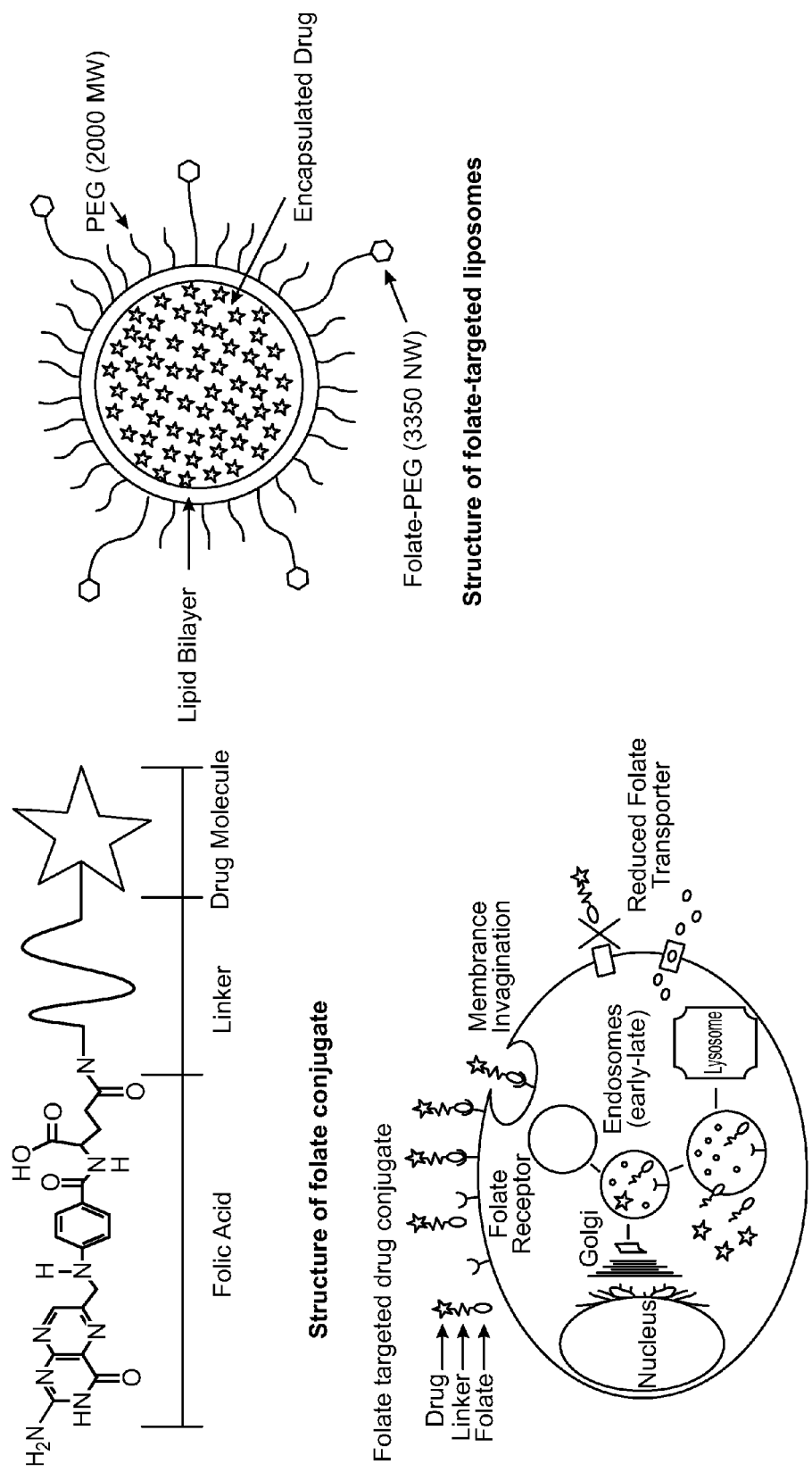
FIG. 5 shows an example where a folate conjugate with a radiolabeled drug as disclosed herein is used to image folate-targeted liposomes.

The compounds, compositions, and methods described herein may be understood more readily by reference to the following detailed description of specific aspects of the disclosed subject matter and the Examples and Figures included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

CHEMICAL DEFINITIONS

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, for example 1 to 3, 1 to 4, 1 to 5, 1 to 6, 1 to 7, 1 to 8, 1 to 9, 1 to 10, or 1 to 15 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms, for example, 2 to 5, 2 to 10, 2 to 15, or 2 to 20 carbon atoms, with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms, for example 2 to 5, 2 to 10, 2 to 15, or 2 to 20 carbon atoms, with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "carbonyl as used herein is represented by the formula —$C(O)Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. Throughout this specification "C(O)" or "CO" is a short hand notation for C=O.

The term "aldehyde" as used herein is represented by the formula —C(O)H.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —$C(O)NZ^1Z^2$.

The term "carboxylic acid" as used herein is represented by the formula —C(O)OH. A "carboxylate" or "carboxyl" group as used herein is represented by the formula —$C(O)O^-$.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions and Methods

Traditional methods of radiolabeling compounds with $^{18}$F involve the formation of a carbon-fluorine bond. Such methods can be time consuming, complex, and inefficient. Methods to $^{18}$F-label compounds should be kept as short as possible. Moreover, the introduction of the radiolabel should occur as late in the synthetic sequence as possible. Still further, the methods should avoid harsh reaction conditions, such as high temperature, high pressure, strong acid or basic condition, and long reactions times, especially when the compound that is being labeled in a biomolecule such as a peptide or protein.

To address these concerns, disclosed are reagents that contain a 1-bora-1-fluoro-2,6,7-trioxabicyclo[2.2.2]octane moiety (shown below) and methods of making and using such a moiety.

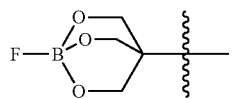

Reagents containing this moiety can be conjugated to therapeutics, peptidomimetics, peptides, proteins, or other biomolecules, which can then be used as PET imaging probes.

The 1-bora-2,6,7-trioxabicyclo[2.2.2]octane has a bridgehead boron and the bicyclic ring strain creates a chelated super Lewis acidic borate ester that readily accepts a fluoride anion. Specifically, the boronate ester has an empty p-orbital that reacts with F anion in aqueous solvent very rapidly to form a stable reagent. The resulting 1-bora-1-fluoro-2,6,7-trioxabicyclo[2.2.2]octane containing reagents are stable for at least about 52 hours in water. Moreover, they are easily prepared and stable for more than 26 half-lives for the positron-emitting $^{18}$F radioisotope that is the most commonly used in PET imaging radioisotope.

1-bora-2,6,7-trioxabicyclo[2.2.2]octane can be prepared from tris(2-amino-2-hydroxymethyl-propane-1,3-diol), which is commercially available. The amino group in tris can be used to attach groups that allow easy conjugation of therapeutics and biomolecules. Thus also disclosed herein are 4-amino-1-bora-1-fluoro-2,6,7-trioxabicyclo[2.2.2]octane containing reagents that have protecting groups and/or linkers attached to the amino group. These reagents can be used to prepare PET imaging probes in 2 steps and less than about 10 minutes.

In specific examples, disclosed are reagents that have Formula I:

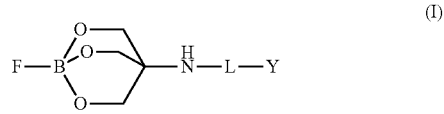

wherein L is a bond or a linker of from 1 to 20 atoms in length; and

Y is a reactive moiety capable of forming a bond with a therapeutic, protein (e.g., enzyme, or antibody), peptide, or other biomolecule.

Linker (L)

As noted herein, the disclosed reagents comprise a reactive moiety (Y) capable of forming a bond with a therapeutic, protein (e.g., enzyme, or antibody), peptide, other biomolecule, or any other molecule one desires to radiolabel, thereby functionalizing said compound with $^{18}$F. The reactive moiety (Y) can be directly attached to the 4-amino-1-bora-1-fluoro-2,6,7-trioxabicyclo[2.2.2]octane moiety, i.e., where L is a bond, or can be attached through a 1-20 atom linker. The linker is shown as L in Formula I. The linker of the disclosed reagents can arise from any compound (linker) that forms a bond with the amino group of the 4-amino-1-bora-1-fluoro-2,6,7-trioxabicyclo[2.2.2]octane moiety and the reactive moiety Y, linking them together. Thus, a linker typically contains at least two functional groups, e.g., one functional group that can be used to form a bond with the 4-amino-1-bora-1-fluoro-2,6,7-trioxabicyclo[2.2.2]octane moiety and another functional group that can be used to form a bond with the reactive moiety Y. Alternatively, the end of the linker can itself be the reactive moiety Y. Typically, though not necessarily, the functional group on the linker that is used to form a bond with the 4-amino-1-bora-1-fluoro-2,6,7-trioxabicyclo[2.2.2]octane moiety is at one end of the linker and the functional group that is the reactive moiety Y or is used to form a bond with the reactive moiety Y is at the other end of the linker.

In a preferred aspect, the linker can comprise electrophilic functional groups that can react with the nucleophilic amine group on the 4-amino-1-bora-1-fluoro-2,6,7-trioxabicyclo[2.2.2]octane moiety, forming a bond. Conversely, the linker can comprise nucleophilic functional groups that can react with electrophilic functional groups like carbonyl, halide, or alkoxyl groups on the reactive moiety Y.

These bonds can be formed by reaction methods known in the art. For example, the 4-amino-1-bora-1-fluoro-2,6,7-trioxabicyclo[2.2.2]octane moiety can be first attached to the linker, followed by attaching the reactive moiety Y. Alternatively, the linker can be first attached to the reactive moiety Y and then attached to the 4-amino-1-bora-1-fluoro-2,6,7-trioxabicyclo[2.2.2]octane moiety. Still further, the 4-amino-1-bora-1-fluoro-2,6,7-trioxabicyclo[2.2.2]octane moiety and reactive moiety can both be attached to the linker simultaneously.

The linker L can be of varying lengths, such as from 1 to 20 atoms in length. For example, the linker L can be from 1, 2, 3, 4, 5, 6, 7, 8, 9, 10, 11, 12, 13, 14, 15, 16, 17, 18, 19, or 20 atoms in length, where any of the stated values can form an upper and/or lower end point of a range. In preferred examples, the linker L can be from 1-10 atoms in length, more preferably from 1-6 atoms in length. Further, the linker L can be substituted or unsubstituted. When substituted, the linker L can contain substituents attached to the backbone of the linker L or substituents embedded in the backbone of the linker L. For example, an amine substituted linker L can contain an amine group attached to the backbone of the linker L or a nitrogen in the backbone of the linker L. Specific substituents on a substituted linker include acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro Suitable linker moieties include, but are not limited to, substituted or unsubstituted, branched or unbranched, alkyl, alkenyl, or alkynyl groups, ethers, esters, polyethers, polyesters, polyalkylenes, polyamines, heteroatom substituted alkyl, alkenyl, or alkynyl groups, cycloalkyl groups, cycloalkenyl groups, heterocycloalkyl groups, heterocycloalkenyl groups, and the like, and derivatives thereof, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro.

In some aspects, the linker moiety can comprise a $C_1$-$C_6$ branched or straight-chain alkyl, such as methyl, ethyl, n-propyl, iso-propyl, n-butyl, iso-butyl, sec-butyl, tert-butyl, n-pentyl, iso-pentyl, neopentyl, or hexyl, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro.

In a specific example, the linker L can comprise —$(CH_2)_m$—, wherein m is from 1 to 10, and where the point of attachment to the 4-amino-1-bora-1-fluoro-2,6,7-trioxabicyclo[2.2.2]octane moiety and/or reactive moiety is an ester, ether, carboxylate, amine, or amide bond. For example, the linker L can be $X^1$—$(CH_2)_m$—$X^2$, wherein m is from 1 to 10, and $X^1$ and $X^2$ are, independent of one another, $CH_2$, C(O), C(O)O, C(O)N, NH, or O.

In still other aspects, the linker L can comprise a $C_2$-$C_6$ branched or straight-chain alkyl, wherein one or more of the carbon atoms are substituted with oxygen (e.g., an ether) or an amino group. For example, suitable linkers can include, but are not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like, and derivatives thereof, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro.

Any of the disclosed linkers L herein can be attached to the amine of the 4-amino-1-bora-1-fluoro-2,6,7-trioxabicyclo[2.2.2]octane by a bond, amide bond, or carbamate bond.

In a preferred example, the linker L is —C(O)CH$_2$CH$_2$C(O)—, i.e., a succinate ester.

Reactive Moiety (Y)

Reagents of Formula I contain an a reactive moiety that is capable of forming a bond with a therapeutic, protein, peptide, or other biomolecule. The reactive moiety can be attached directly to the 4-amino-1-bora-1-fluoro-2,6,7-trioxabicyclo[2.2.2]octane moiety, i.e., where L is a bond, or through a linker L.

In some examples, the reactive moiety can be an amino acid residue, such as shown in Table I. It is also understood that protected derivates of these amino acids, such as Cbz, Fmoc, and t-Boc derivatives, and the like, can be used.

TABLE 1

| Amino Acid Abbreviations | |
|---|---|
| Amino Acid | Abbreviations |
| Alanine | Ala (A) |
| allosoleucine | AIle |
| Arginine | Arg (R) |
| asparagine | Asn (N) |
| aspartic acid | Asp (D) |
| Cysteine | Cys (C) |
| glutamic acid | Glu (E) |
| glutamine | Gln (K) |
| Glycine | Gly (G) |
| Histidine | His (H) |
| isolelucine | Ile (I) |
| Leucine | Leu (L) |
| Lysine | Lys (K) |
| phenylalanine | Phe (F) |
| methionine | Met (M) |
| Proline | Pro (P) |
| pyroglutamic acid | PGlu |
| Serine | Ser (S} |
| threonine | Thr (T) |
| Tyrosine | Tyr (Y) |
| tryptophan | Trp (W) |
| Valine | Val (V) |

The amino acid can be attached to the 4-amino-1-bora-1-fluoro-2,6,7-trioxabicyclo[2.2.2]octane moiety directly or the linker L by its amino group, thus leaving the carboxylic acid group or other reactive side chain available for attachment to the therapeutic, protein, peptide, or other biomolecule. Alternatively, the amino acid can be attached to the 4-amino-1-bora-1-fluoro-2,6,7-trioxabicyclo[2.2.2]octane moiety directly or the linker L by its carboxylic acid group, thus leaving the amino group or other reactive side chain available for attachment to the therapeutic, protein, peptide, or other biomolecule. Alternatively, the amino acid can be attached to the 4-amino-1-bora-1-fluoro-2,6,7-trioxabicyclo[2.2.2]octane moiety directly or the linker L by its side chain, thus leaving the carboxylic acid group and/or amino group available for attachment to the therapeutic, protein, peptide, or other biomolecule.

In other examples, the reactive moiety is a functionalized aryl or heteroaryl group. Thus, Y can be:

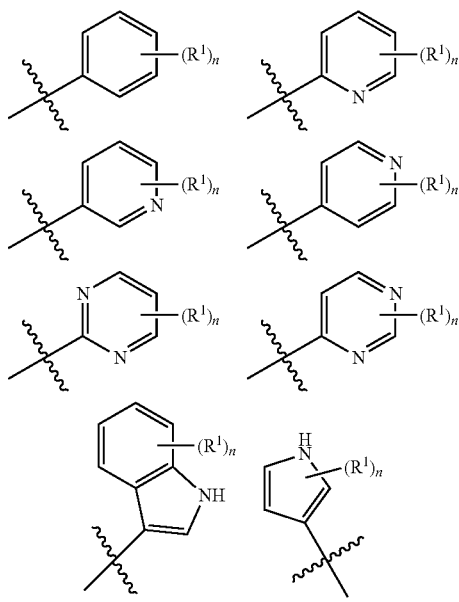

where n is 1, 2, 3, 4, or 5; and
each R¹, independent of the others, is halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl.

In a specific example, the linker L can reactive group Y can together be 4,4'-propane-2,2-diyldiphenyl.

In still further examples, the reactive moiety Y can be an aldehyde, acyl azide, acyl nitrile, succinimidyl ester, sulfosuccinimidyl ester, anhydride, mixed anhydride, carboxylic acid or carboxylate, epoxide, imine, isocyanate, isothiocyanate, sulfonyl chloride, halogen, or maleimide. Alternatively, the reactive moiety can be a hydrazine, amine, amide, alcohol, or thiol.

When the reactive moiety Y is or contains a carboxylate or ester it can, depending on the conditions, be slow to react with a therapeutic, protein, peptide, or other biomolecule. However, these reactive moieties can be converted into more reactive, activated esters by a carbodiimide coupling with a suitable alcohol, e.g., 4-sulfo-2,3,5,6-tetrafluorophenol, N-hydroxysuccinimide or N-hydroxysulfosuccinimide. This results in a more reactive, water-soluble activated ester moiety. Various other activating reagents that can be used and include, but are not limited to, 1-ethyl-3-(3-dimethylaminopropyl) carbodiimide (EDC), dicyclohexylcarbodiimide (DCC), N,N'-diisopropyl-carbodiimide (DIP), benzotriazol-1-yl-oxy-tris-(dimethylamino)phosphonium hexa-fluorophosphate (BOP), hydroxybenzotriazole (HOBt), and N-methylmorpholine (NMM), including mixtures thereof).

PET Imaging Probes

The disclosed reagents can be used to radiolabel a therapeutic, protein, peptide, biomolecule or any other molecule that one desires to label with ¹⁸F. Such radiolabeled compounds can be used a probes in PET based examinations, diagnoses, and studies. The process for radiolabeling molecules is shown in the following general scheme:

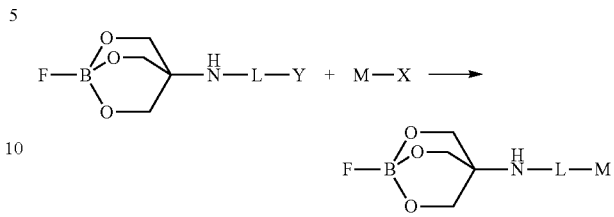

where L and Y are as defined previously, and M is a therapeutic, protein, peptide, biomolecule, or other molecule of interest that one seeks to label. X represents a reactive moiety on M that will react with reactive moiety Y and form a bond, resulting in a bond(s) between the 4-amino-1-bora-1-fluoro-2,6,7-trioxabicyclo[2.2.2]octane moiety and the molecule of interest. In other example, the molecule M can be attached to a solid phase support.

In certain examples, when the molecule M is a protein, such as an enzyme or antibody, a peptide, peptidomimetic, or any fragment that contains a carboxylic acid or carboxylate group, a carbodiimide-mediated coupling can be used to form a bond between the linker or 4-amino-1-bora-1-fluoro-2,6,7-trioxabicyclo[2.2.2]octane moiety and the molecule M. For example, a linker L with a hydrazine or amine group as Y can be coupled to an molecule M with a carboxylate or carboxylic acid functional groups (i.e., X) using water-soluble carbodiimides such as 1-ethyl-3-(3-dimethylaminopropyl)carbodiimide. Suitable reactive groups Y capable of carbodiimide-mediate coupling to carboxylate or carboxylic acid containing molecules M are commercially available. Specific examples include, but are not limited to, water soluble carbodiimides such as 1-ethyl-3-(3-dimethylaminopropyl)-carbodiimide HCl and 1-cyclohexyl-3-(2-morpholinoethyl)-carbodiimide-metho-p-toluene sulfonate, alcohol and water soluble N-ethyoxycarbonyl-2-ethoxy-1,2-dihydroquinoline, and organic soluble N,N'-dicyclohexylcarbodiimide.

In an alternative aspect involving a carbodiimide-mediated coupling, a linker L with a carboxylate or carboxylic acid group Y can be coupled to a molecule M with amine functional groups X using water-soluble carbodiimides such as 1-ethyl-3-(3-dimethylaminopropyl)-carbodiimide.

In other examples, the linker with an amine, hydroxy, or thiol as Y can be used in a substitution reaction with a molecular M having a leaving group X as, e.g., halogen, mesylate, tosylate, triflate, and the like.

The result of the radiolabeling process can have a structure as shown below:

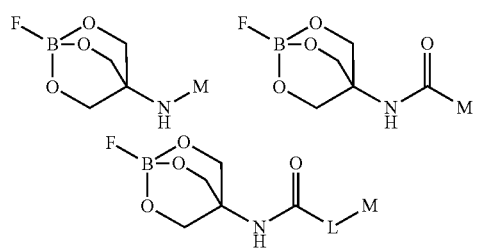

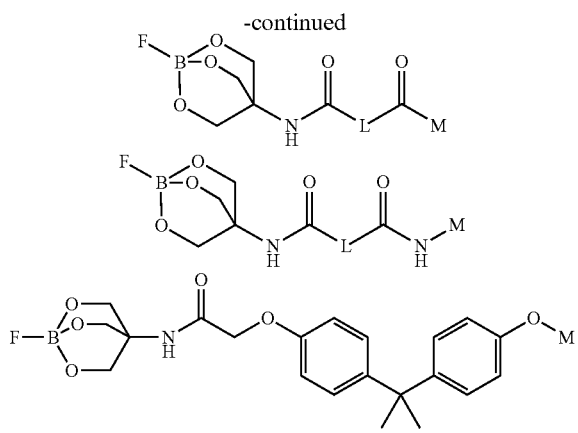

where L and M are as defined herein.

Some specific examples of molecules of interest M that can be radiolabled with the reagents and by the methods disclosed herein include 105A5; 11-1F4; 16alpha,17alpha-dioxolane progestin analogs (breast cancer); 28A32; 3E8; 5-aminolevulinic acid hydrochloride (glioma imaging); 6-FPOL; 6-Me-BTA-1; A20FMDV2; A33; A-84543; AB-3025-11; ABD-035; Abdoscan; ABY-025; ABY-026; ABY-028; acetylcholinesterase (AChE) inhibitors (Alzheimer's disease); Adenoscan; adrenomedullin (pulmonary disease); AGT-100; AGT-160; AH113804; Albunex; alpha-7 nicotinic receptor binding PET ligands (neurological disorders); Altropane; AMBA; AMG-655; AMI-121; AMI-25; AMI-HS; amyloid binding PET ligands (Alzheimers disease); ANA-5 analog (oral radiolabeled imaging agent, Alzheimers disease); androgen receptor modulators (imaging, cancer); AnnAl IgG; annexin V-128 (rheumatoid arthritis/Crohn's disease); anti PSA antibody conjugates (prostate cancer therapy/diagnosis); anti-CEACAM6 antibodies; anti-ED-B antibody; anti-PSMA huJ591 minibodies; antimelanoma antibodies; antisense oligonucleotide CDK inhibitor imaging agent; anti-tPA antibody; anti-ZnT8 antibody (diabetes); AP(4)A; AP-2011; apadenoson; apcitide; arcitumomab; AT-004; atrasentan PET imaging agent (cancer); atrial natriuretic peptide; ATSM; AVP-4; AVP-5; AVP-6; AVP-7; AZD-2995; AZD-2184; AZD-4694; azetidinylmethoxypyridine (nervous system imaging); AZPET; B3; SRVII23; BAY-1006451; BAY-1006578; BAY-1075553; BAY-1163615; BAY-85-8102; BAY-86-4367; BAY-86-4884; BAY-86-7548; BAY-86-9596; BChE inhibitors (imaging, Alzheimers disease); BCI-632; Benzyl-DTPA-Z(HER2:342)-pep2; besilesomab; betafectin; beta1-adrenoceptor-targeted imaging agents (cardiovascular disease); BFPET; binodenoson; bivalirudin (nanoparticle, thrombosis); BMIPP; BMS-753951; BOT-502; BR-14; BR-55; BT-19; BT-20; BT-23; BW-42; BY-963; Capiscint; capromab pendetide; carbonic anhydrase IX inhibitors (cancer, imaging); CardioPET; carfentanil; Cavisomes; CB1 antagonists (brain imaging); cell penetrating peptide (diagnostic, cancer) CDG; CEN-109; CGRP-A2 (migraine); chlorin-e6-conjugated mucin-targeted aptamers (photodynamic therapy/imaging, cancer); chTNT-1/B; CI 1-SB-207145; CIM-ANT; ciprofloxacin; CLR-1404; CMICE-013; DCF-PyL; demogastrin 2 (medullary thyroid cancer); depreotide; DIATHIS-1; dopamine antagonist (Parkinsonistic features); DRM-106; DTPA; DTPA-Glipizide; EC-0652; EC-DG; EC-G; EC-metronidazole; eptacog alfa (bleeding); ETS; exendin derivatives (imaging GLP-1 receptors, diabetes); fanolesomab; GLP-1 analogs (neuroendocrine tumor imaging); glucarate; GSK-215083; HSV1-tk (cancer); Hynic-Annexin V; ICF-01006; IMPY; iodobenzamide; iodometomidate; iofetamine; ioflupane; iomazenil; iometopane; lactam bridge-cyclized alpha-melanocyte-stimulating hormone peptide (melanoma); leukotrine B4 antagonist; LFA-1 targeted imaging agent (lymphoma/leukemia); LY-2795050; MAG3-HER2/MUC1 peptide (breast cancer); maraciclatide; MAS3-TM-601; MePPEP; Met; MFE-23; MIBG; MIBG; MICA; MIP-1340; MIP-1404; MIP-1405; MIP-1407; MK-3168; MK-8278; MNI-168; MNI-330; MNI-420; MSA; N4-Tyrosine; NC-100668; N-DBODC5; nitrocade; nitroimidazole; nociceptin/orphanin FQ receptor PET ligands (neuropsychiatric disorders); nofetumomab; NP-50511; NS-2381; NSI-1; NVLS/FMAU; NVLS/FX-18A; OBP-401; octafluoropropane; OctreoScan; oligonucleotide (FINE); onartuzumab (imaging, cancer); Oncotec; Oralex; OvaFluor; oxidronic acid; oxilan; P215; P-3378; P424; P483H; P587; P748; P-773; P-947; PB-127; Pb-203 labeled [DOTA]-ReCCMSH targeted alpha particle-emitting radionuclides (cancer); PBR-170; PBR-28; PCP-Scan; PDL-506; Pentacea; Pepscan; perflexane-lipid microsphere; perflubutane (lipid microsphere-encapsulated, imaging); perflubutane (polymer microsphere-encapsulated, heart disease); perflutren lipid microsphere; PGN-650; PIMBA; Prognox; ProScan-A; ProstaFluor; ProstaLite; Prostatec; Prostaview; PSCA targeting minibody (cancer); PSMA inhibitors (prostate cancer, imaging); PT-16; PTSM; pyridyl benzofuran derived imaging agent (nervous system disorder); Quantison; QW-7437; R-129144; anti-CD4 monoclonal antibody fragment (imaging agent, chronic inflammation); radretumab; rBitistatin; recombinant TSH superagonists (thyroid cancer); rituximab (cancer); rotenone (cardiac perfusion); RP-128; RU-40555; seglitide; sestamibi; siboroxime; sigma opioid receptor ligands; sigma-2 receptor ligands (solid tumor); sulesomab; teboroxime; tetrofosmin; TM-601; TM-601; TP-3805; TP-850; TR-21; tropantiol; VEGF (cancer); VEGFR-1 inhibitors (cancer); WC-10 (neurological disease).

In preferred examples, the molecule M can be selected from ISO-1; ethanolamine derivatives (cancer imaging); AV-45 dimer; BAY-85-8050; FDDNP; FEDAA-1106; FEPPA; fluoromethylallylcholine; flutabine; F-PEB; FRP-170; fluoropolyethylene glycol derivatives (Alzheimers disease detection); glyburide analogs; nAChR antagonists (Alzheimers disease); mGlu-5 tracers; MNI-558; NST-ML-10; SKI-696; SMIBR-K5; SMIBR-W372; VEGF binding peptides; ErbB-2 receptor targeting peptides (cancer); florbenazine; florbetaben; florbetapir; florilglutamic acid; fluciclatide; fluoratec; fluoropegylated indolylphenylacetylenes (Alzheimer's disease); flurpiridaz; flutemetamol; and folate. The molecule M can also be FDEGPECO, which is a tracer for imaging the metabotropic glutamate receptor subtype 5 (mGluR5). In general, almost any molecule with reactive groups can be conjugated to the disclosed reagents to prepare a PET imaging probe.

Figure 6:
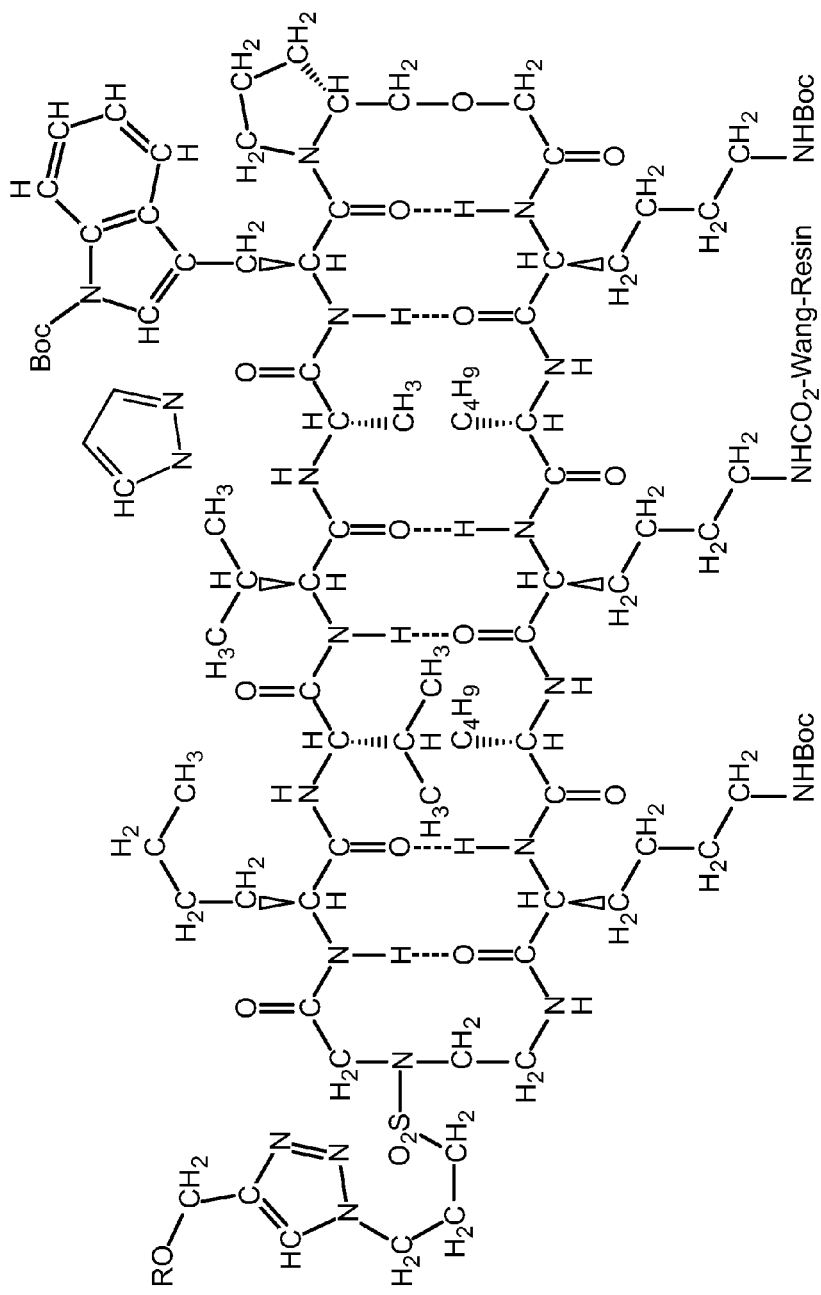
FIG. 6 shows a cyclic peptidomimetic MTI-101 attached to a solid support and functionalized with a reagent as disclosed herein.
Figure 6:
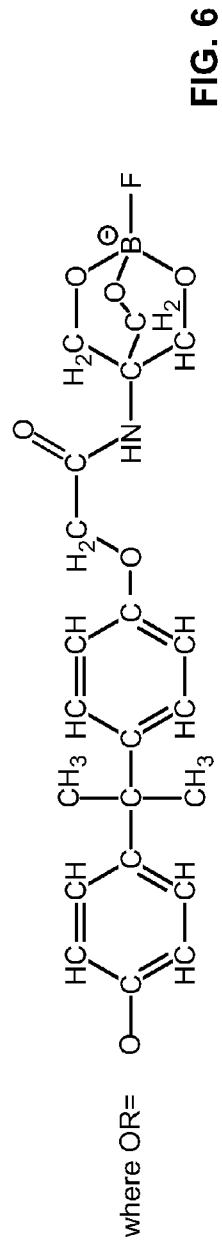

In one particular example, the disclosed reagents are used to radiolabel MTI-101, which is a cyclic peptidomimetic. The coupling reaction can be performed on a solid phase as shown in FIG. 6. The resulting PET imaging probe can be a very useful agent for imaging myeloma tumors in the bone in animals and humans. Disclosed is a method of using the PET probes herein as a specific myeloma bone tumor PET imaging agent based on MTI-101 binding to CD44.

Compositions, Formulations and Methods of Administration

In vivo administration of the disclosed compounds, and compositions containing them, can be accomplished by any suitable method and technique presently or prospectively known to those skilled in the art. For example, the disclosed compositions or probes can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compositions or probes can be a single administration, or at continuous or distinct intervals as can be readily determined by a person skilled in the art.

The compositions or probes disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compositions or probes disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compositions or probes disclosed herein can be formulated such that an effective amount of the composition or probe is combined with a suitable carrier in order to facilitate effective administration of the drug. The resulting compositions can be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the disclosed composition or probe based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compositions or probes disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. The compositions or probes can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

In certain examples, the compositions or probes disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compositions or probes disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compositions or probes can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compositions or probes disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compositions or probes disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a compositions or probes disclosed herein can be applied in as a liquid or solid. However, it will generally be desirable to administer them topically to the skin as compositions, in combination with a dermatologically acceptable carrier, which can be a solid or a liquid. Compositions disclosed herein can be applied topically to a subject's skin to reduce the size (and can include complete removal) of malignant or benign growths, or to treat an infection site. Compositions or probes disclosed herein can be applied directly to the growth or infection site. Preferably, the compositions or probes is applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the conjugates, nanotubes, and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

What is claimed is:

1. A reagent for radiolabeling a molecule having Formula I:

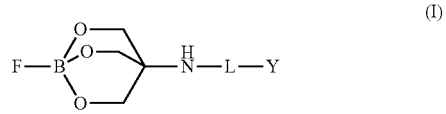

wherein F is $^{18}$F, L is a bond or a linker of from 1 to 20 atoms in length and Y is a reactive moiety capable of forming a bond with another molecule.

2. The reagent of claim 1, wherein L is a linker from 1-10 atoms in length.

3. The reagent of claim 1, wherein L is a substituted or unsubstituted, branched or unbranched, alkyl, alkenyl, or alkynyl group, ether, ester, polyether, polyester, polyalkylene, polyamine, heteroatom substituted alkyl, alkenyl, or alkynyl group, cycloalkyl group, cycloalkenyl group, heterocycloalkyl group, or heterocycloalkenyl group, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro.

4. The reagent of claim 1, wherein L is a $C_1$-$C_6$ branched or straight-chain alkyl, or a $C_2$-$C_6$ branched or straight-chain alkyl, wherein one or more of the carbon atoms are substituted with oxygen or an amino group, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro.

5. The reagent of claim 1, wherein L is $X^1$—$(CH_2)_m$—$X^2$, wherein m is from 1 to 10, and $X^1$ and $X^2$ are, independent of one another, $CH_2$, $C(O)$, $C(O)O$, $C(O)N$, NH, or O.

6. The reagent of claim 1, wherein L is —$C(O)CH_2CH_2C(O)$—.

7. The reagent of claim 1, wherein Y is a protected or unprotected alanine, allosoleucine, arginine, asparagine, aspartic acid, cysteine, glutamic acid, glutamine, glycine, histidine, isoleucine, leucine, lysine, phenylalanine, methionine, proline, pyroglutamic acid, serine, threonine, tyrosine, tryptophan, or valine.

8. The reagent of claim 1, wherein Y is an aldehyde, acyl azide, acyl nitrile, ester, succinimidyl ester, sulfosuccinimidyl ester, anhydride, mixed anhydride, carboxylic acid, epoxide, imine, isocyanate, isothiocyanate, sulfonyl chloride, halogen, maleimide, hydrazine, amine, amide, alcohol, carboxylate, or thiol.

9. The reagent of claim 1, wherein Y has a formula chosen from:

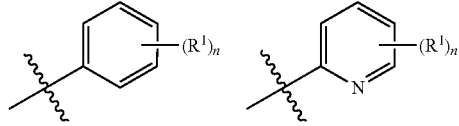

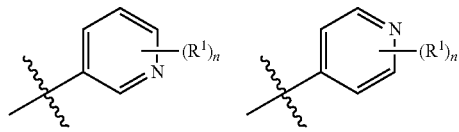

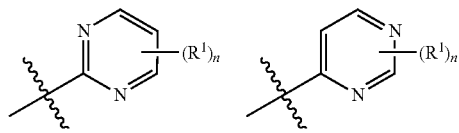

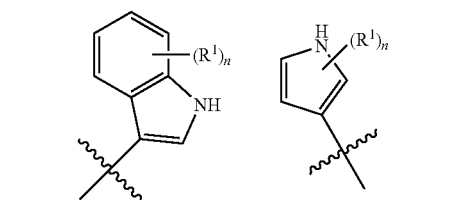

where n is 1, 2, 3, 4, or 5; and each R¹, independent of the others, is halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl.

10. The reagent of claim 1, wherein the reagent has a formula chosen from:

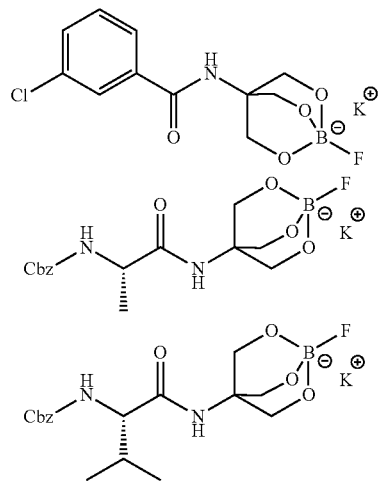

-continued

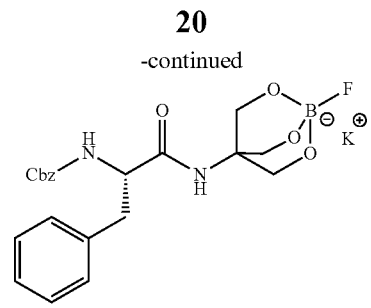

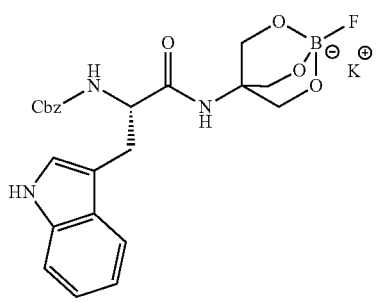

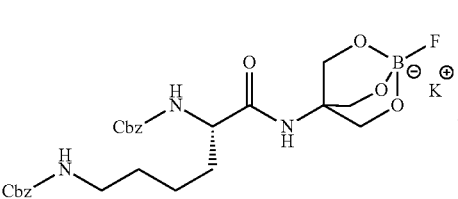

11. The reagent of claim 1, wherein the reagent has a formula chosen from:

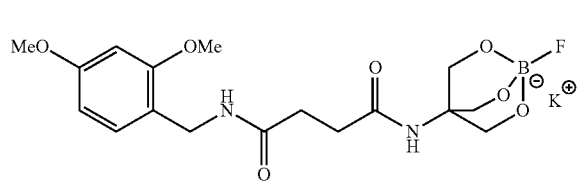

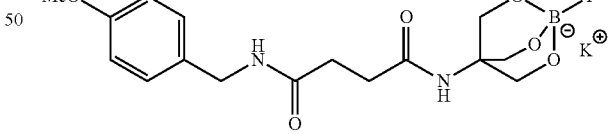

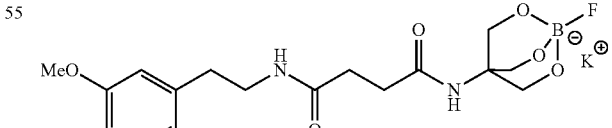

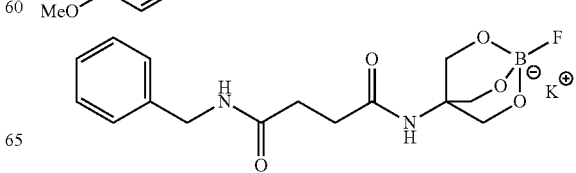

-continued
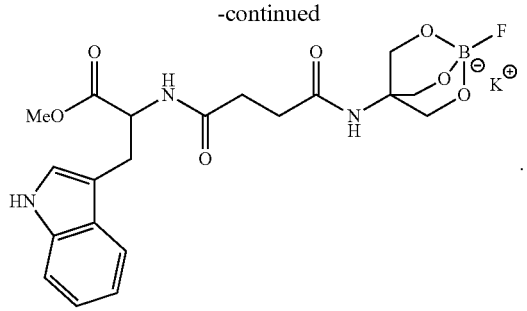
* * * * *